United States Patent [19]

Heinonen

[11] Patent Number: 5,182,618
[45] Date of Patent: Jan. 26, 1993

[54] REFLECTOMETRIC METHOD OF MEASUREMENT AND APPARATUS FOR REALIZING THE METHOD

[76] Inventor: Aimo Heinonen, Örkkiniityntie 19, SF-02970 Espoo, Finland

[21] Appl. No.: 793,261

[22] Filed: Nov. 13, 1991

Related U.S. Application Data

[63] Continuation of Ser. No. 512,020, Apr. 16, 1990, abandoned, which is a continuation of Ser. No. 296,348, Jan. 9, 1989, abandoned, which is a continuation of Ser. No. 934,949, Nov. 26, 1986, abandoned.

[30] Foreign Application Priority Data

Nov. 27, 1985 [FI] Finland .................... 854700

[51] Int. Cl.$^5$ ............... G01N 21/47; G01J 1/00; G01T 1/00
[52] U.S. Cl. ................... 356/446; 250/228; 356/448
[58] Field of Search ........... 356/445, 446, 447, 448, 356/236; 250/228

[56] References Cited

U.S. PATENT DOCUMENTS

| | | | |
|---|---|---|---|
| Re. 27,270 | 1/1972 | Selgin ................... | 356/211 |
| 2,766,653 | 10/1956 | Martin et al. ........... | 88/14 |
| 3,340,764 | 9/1967 | Bergson ................ | 88/14 |
| 3,476,482 | 11/1969 | Howard et al. ......... | 356/199 |
| 3,609,045 | 9/1971 | Stein .................... | 356/448 X |
| 3,817,628 | 6/1974 | Adams .................. | 356/448 |
| 3,827,808 | 8/1974 | Cho ...................... | 356/236 X |
| 3,874,799 | 4/1975 | Isaacs et al. ........... | 356/236 X |
| 4,455,090 | 6/1984 | Roberts ................. | 356/448 |
| 4,539,647 | 9/1985 | Kaneko et al. ......... | 356/446 X |

FOREIGN PATENT DOCUMENTS

| | | |
|---|---|---|
| 351295 | 7/1979 | Austria . |
| 3413838 | 4/1984 | Fed. Rep. of Germany . |
| 2013334 | 1/1979 | United Kingdom . |

OTHER PUBLICATIONS

"Farbe Unde Lack", 1980, vol. 7, pp. 595-597.

*Primary Examiner*—Paul M. Dzierzynski
*Assistant Examiner*—Michael B. Shingleton
*Attorney, Agent, or Firm*—Andrus, Sceales, Starke & Sawall

[57] ABSTRACT

A reflectometric method of measurement for a 2-channel reflectometer, wherein in connection with the calibration, the standard sample is placed in the measruing channel (4), the dimming of the measuring channel is set to a random position and the light intensities detected both in the measuring channel and the reference channel (14) are adjusted into balance by adjusting the dimming of the reference channel by aid of the measuring diaphragm (17), and the measuring of the sample is carried out by setting the intensities into balance, likewise by aid of the measuring diaphragm of the reference channel. The reflectance value of the sample under measurement is calculated from the reflectance value of the standard, by aid of the set value of the measuring diaphragm obtained in the measurement and on the basis of the set value of the measuring diaphragm obtained in the calibration measurement.

4 Claims, 2 Drawing Sheets

REFLECTOMETRIC METHOD OF MEASUREMENT AND APPARATUS FOR REALIZING THE METHOD

This application is a continuation of Ser. No. 07/512,020, now abandoned filed Apr. 16, 1990, which is a continuation of Ser. No. 07/296,348, filed Jan. 9, 1989, now abandoned, which is a continuation of Ser. No. 06/934,949, filed Nov. 26, 1986, now abandoned.

The present invention relates to a reflectometric method of measurement. Moreover, the invention relates to a measuring apparatus for reflectometric measurements.

BACKGROUND OF THE INVENTION

A particular object of the invention is a reflectometric method of measurement and a corresponding apparatus where the sample to be measured is diffusely illuminated. In the prior art such a method and apparatus are called Elrepho (short for Electric Reflectance Photometer). Reflectometric methods of measurement are employed while measuring the whiteness, fluorescence, brightness, transparency, opacity and clarity of the samples, or other such reflectometric optical properties. An even more specified object of the invention is a reflectometric method of measurement and apparatus for measuring the ISO (International Standard Organisation) whiteness in paper, pulp and paper-board, i.e. in various paper products.

Nowadays paper whiteness is practically everywhere measured almost exclusively by using the two-channel reflectometric measuring apparatus manufactured by Zeiss. The apparatus comprises a ball-like measuring chamber which is white inside and is provided with two channels, i.e. microscopes complete with diaphragms, and a sample aperture and a standard sample aperture, placed respectively in line with the channels, the measuring channel and the reference channel. The light intensities in the channels are detected by means of photometers located in the channels, and the light intensities in the channels are observed by means of a galvanometer, whereto the photometers are connected. The apparatus is calibrated so that the standard sample with a known reflectance value is placed in the reference channel, and the measuring diaphragm of the reference channel is set to correspond to the known reflectance value of the standard sample. Thereafter the diaphragm of the measuring channel is adjusted so that the light intensities are equally strong, i.e. in equilibrium in both channels. The reflectance value of the sample to be measured is defined by placing the sample in the measuring channel and by adjusting the measuring diaphragm in such a position that the two channels are in balance; now the reflectance value of the sample can be read on the scale of the measuring diaphragm. During the measurement of the sample, the diaphragm of the measuring channel is kept in the position adjusted in the calibration measurement.

The above described prior art method and apparatus for reflectometric measurements have, however, proved to be unsatisfactory as the demands for the accuracy of the measurements have grown. Particularly the adjusting of the diaphragm in the measuring channel—whereby the channels are set in balance and the scale of the measuring diaphragm in the reference channel is defined in connection with the calibration—is inaccurate; in other words, the accuracy of the adjustment is dependent on the operator and his personal accuracy. Moreover, the described adjusting of the diaphragm in the measuring channel must be carried out anew for almost every measurement.

Furthermore, the scale of the measuring diaphragm of the reference channel is based on the scale of measurement engraved in the measuring diaphragm while the device has been manufactured, which scale is only set to a desired level during the calibration by aid of a standard sample. Consequently, for instance when the measuring equipment becomes aged, the deviation between measuring results from separate apparatuses is increased, and the measuring results thus become unreliable.

Moreover, the above described method and apparatus of measurement are based on the presupposition that the reflectance values of the samples are linearly dependent on the position of the measuring diaphragm, i.e. that the scale of the measuring diaphragm is made linear. However, thorough measurements have shown that the reflectance values of different samples do not change in a linear fashion along with the adjusting of the dimming. Consequently, erroneous results in measurement are inherent already in the structure of the method and apparatus of the prior art.

Owing to the above explained and other reasons, the reflectometric methods and apparatuses currently in use have proved out to be largely unsatisfactory. Thus for instance reflectance measurements of paper, carried out both by the manufacturer and the purchaser, have given considerably differing results—in other words, the measuring methods and apparatuses do not render reproducible, comparable results. In practice the lack of reproducible and comparable results in reflectance measurements has for instance lead to situations where paper batches have been returned to the mill, although both the buyer and the dealer have in turn checked that the particular batch fulfils the requirements as regards the reflectance measurements.

SUMMARY OF THE INVENTION

The object of the present invention is to eliminate the above mentioned drawbacks. A specific object of the invention is to introduce a reflectometric method of measurement and a measuring apparatus, rendering reproducible and comparable results which are remarkably more accurate than in the prior art.

Another object of the invention is to introduce a reflectometric method of measurement and a measuring apparatus by aid of which the measurements can be carried out considerably more swiftly and securely than before, so that the accuracy of the operating person affects the final results remarkably less than before.

Yet another object of the invention is to introduce a new reflectometric method of measurement which can be realized mainly by utilizing the prior art Elrepho measuring apparatus currently in general use. Likewise, an object of the invention is to introduce a reflectometric measuring apparatus which can be constructed around a prior art Elrepho apparatus by means of additional components.

Consequently, the overall object of the present invention is to introduce a new reflectometric method of measurement which is suited for various different measurements of the reflectometric type and which is essentially more accurate than the prior art methods, the results of which are essentially better reproducible and more reliable than in the prior art, which method can be realized in a simplier and quicker fashion than in the prior art, and which method in operation is not so sensitive to exterior circumstances as the prior art methods.

As for the characteristic novel features of the invention, reference is made to the appended patent claims.

The invention is based on the basic principle that the measuring channel and the reference channel are set in an exact equilibrium, both during the calibration measurement and the sample measurement, by aid of the measuring diaphragm of the reference channel. In the prior art Elrepho measuring devices, the measuring diaphragm of the reference channel is structurally much more precise than the diaphragm of the measuring channel, which is generally formed of a wedge-like "grey wedge" diaphragm. The present invention makes the calibration measurement essentially more accurate than before. If it is desired that the measuring channel be set in a position corresponding to the light-intensity balance between the two channels, this can of course be carried out in an approximate fashion by aid of the diaphragm of the measuring channel, whereafter the precision adjustments are made by aid of the diaphragm of the reference channel.

The present invention makes it possible that the whole scale of measurement in the reference channel, i.e. the scale of the measuring diaphragm for the sample measurement, and the setting of the measuring scale, is completely defined in connection with the calibration measurements. If desired, a number of separate standard samples can be employed, for instance along the whole scale of the measuring diaphragm, such as near the 0% reflectance, at the 50% reflectance, near the 100% reflectance and, if so desired, at other points of the scale too, in which case the dependence of the reflectance on the scale of the measuring diaphragm can be for example graphically defined for the sample measurements proper.

In a preferred embodiment of the invention, there is employed a control unit which adjusts the position of the diaphragm and the measuring diaphragm automatically, for instance under control of a computer. The central control unit advantageously calculates the reflectance values of the sample on the basis of the measurements carried out under its control.

Furthermore, the employed central control unit can be arranged to control the filters used in the measuring and reference channels so that the measurements can be carried out at a desired wavelength.

Moreover, the central control unit can be arranged to adjust for instance the diaphragm of the measuring channel into a reproducible position which is defined in connection with the calibration measurements and which is to be reproduced in later sample measurements.

The measuring diaphragm of the reference channel and/or the diaphragm of the measuring channel can advantageously be provided with a stepping motor for adjusting the said diaphragms. In that case, when for example a linear stepping precision motor is employed, a motion of the diaphragm corresponding to the whole scale (100%) of the measuring diaphragm, is achieved for instance by means of 10000 control impulses. Thus each impulse, i.e. the smallest adjustable interval in the scale, corresponds to a reflectance of 0.01%. The same rule can be applied both in the reference and the measuring channels.

By using the method and apparatus of the invention, the accuracy gained in performance tests has increased up to 0.001% when computerized control and a stepping impulse motor have been employed for adjusting the diaphragms of the reference channel and the measuring channel. The accuracy gained by using the prior art methods has been at best a questionable 0.3%. By aid of the method and apparatus of the invention the choice of filters, adjustments, the calibration of the scale and the sample measurement proper can all be carried out in an essentially shorter time, which is for example 1/10 of the time required for measurements with prior art equipment. The method and apparatus of the invention are thus absolutely superior in comparison with any prior art arrangements.

DESCRIPTION OF THE DRAWINGS

In the following the invention is explained in more detail in the light of a preferred embodiment and with reference to the appended drawings, where.

DESCRIPTION OF THE ILLUSTRATED EMBODIMENT

Figure 1:
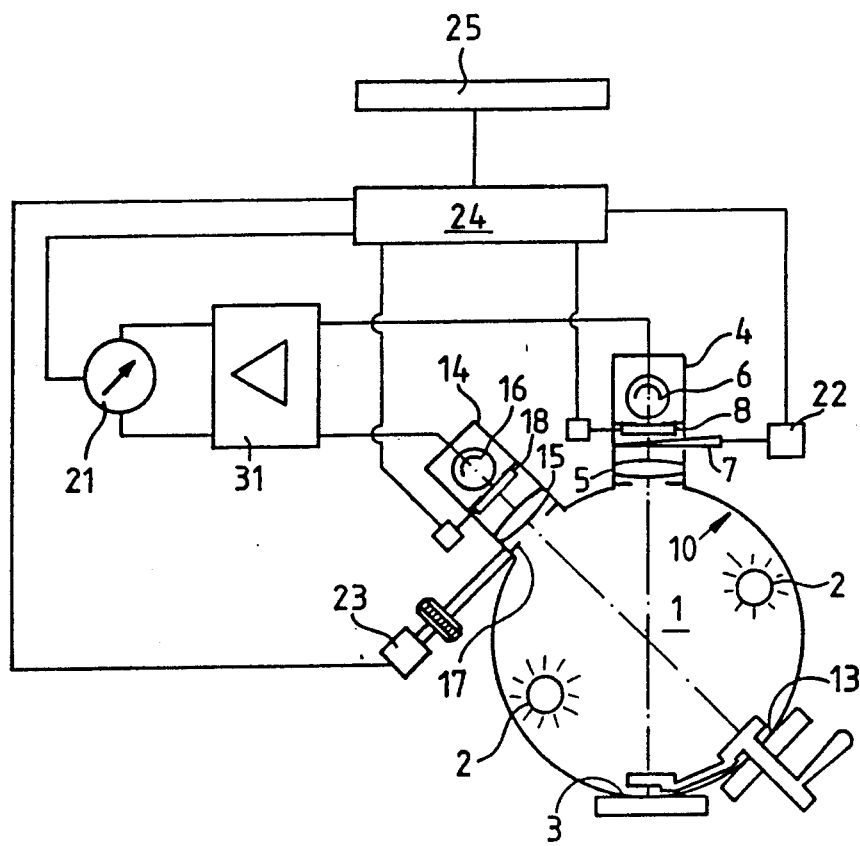
FIG. 1 illustrates a preferred embodiment of the measuring apparatus of the invention and FIG. 2 is a block diagram illustrating the realization of an application of the method of the invention.

FIG. 1 illustrates the measuring apparatus of the invention designed for reflectometric measurements. The apparatus comprises a ball-shaped measuring chamber 1, which in this preferred embodiment is provided with two light sources 2, a sample aperture 3, and—in this embodiment—also a reference aperture 13 for the comparing standard. The inner surface 10 of the measuring chamber 1 is white so that the sample located in the sample aperture 3 is diffusely illuminated.

Moreover, the apparatus comprises a measuring channel 4 and a reference measuring channel 14, both provided with optics 5 and 15 respectively, in order to direct the light reflected to the photometers 6 and 16 pertaining to the corresponding measuring channel and reference channel. Furthermore, the measuring channel 4 and the reference channel 14 are furnished with a diaphragm 7 and a measuring diaphragm 17 respectively, in order to dim the light directed to the photometers 6 and 16 respectively, and possibly with filters 8 and 18 respectively in order to filter the light directed to the photometer. In addition to this, the apparatus comprises a reference measuring device 21 which is arranged to compare the voltages created by the light in the photometers and to indicate the balance between the light intensities in the channels. The reference measuring device 21 comprises an amplifier 31 for improving the reference accuracy.

According to the invention, the diaphragm 7 of the measuring channel 4 and the measuring diaphragm 17 of the reference channel 14 are provided with electric motors 22 and 23 respectively in order to adjust the diaphragms. Furthermore, the measuring apparatus comprises a registering and calculating control unit 24. The control unit is arranged to adjust, during the calibration measurement, the diaphragm 7 of the measuring channel 4 into a random reproducible position, and the measuring diaphragm 17 of the reference channel 14 to a position indicated by the reference measuring device 21, which position conforms to the balance of the light intensities in the channels while the standard sample is placed in the measuring channel. Moreover, the control unit 24 is arranged to adjust, during the sample measurement, the measuring diaphragm 17 of the reference channel 14 similarly to a position conforming to the balance of the light intensities in the channels while the sample to be measured is placed in the measuring channel, i.e. in the sample aperture 3. Further, the registering and calculating control unit 24 is arranged to register the readings of the diaphragms 7 and 17 of the measuring channel 4 and reference channel 14 respectively in connection with the calibration and sample measurements as well as to calculate the reflectance value of the measured sample by aid of the reading of the measuring diaphragm of the reference channel, obtained in the sample measurement, from the reflectance value of the standard value of the standards sample on the basis of the reading of the measuring diaphragm determined in the calibration measurement. The control unit 24 is suitably arranged to perform the standard measurement automatically according to orders from the keyboard 25. Moreover, the control unit 24 is arranged to register the readings of the diaphragm 7 of the measuring channel 4 in accordance with the calibration measurement of the standard sample in use at any given occasion, and respectively to adjust the measuring diaphragm 17 of the reference channel 14 to a respective position, i.e. to a position corresponding to the measurement of the standard sample in question. Now the calibration of the apparatus can be carried out mainly instantaneously under control of the control unit 24. The essential point is the use of adjusting devices for the diaphragms, by aid of which devices the diaphragms can be reproducibly adjusted to a certain position, registered for instance in connection with the calibration or otherwise.

In addition to this, the apparatus may comprise filters for the measuring channel 4 and the reference channel 14; only an identical pair of filters, 8 and 18 respectively, is illustrated in the drawing. The control unit is arranged to shift the filters, by aid of the actuators, into the measuring and reference channels respectively, in accordance with the respective filters employed in the calibration. Thus the apparatus may be provided with a large number of different filters, which the control unit 24 is programmed to guide and adjust into place.

The adjusting motor 23 of the measuring diaphragm of the reference channel 14 is suitably formed of stepping impulse motors of a conventional tupe, which motors are controlled by aid of control impulses. The whole scale of measurement of the reflectometric measuring apparatus, i.e. 100%, may correspond for instance to 1,000, 5,000, 10,000, 20,000, 50,000 or even 100,000 impulses. In that case, the accuracy obtained at the given interval is between 1/10–1/1,000%. Likewise, the adjusting motor 22 of the diaphragm 7 of the measuring channel 4 may be formed of a respective stepping impulse motor.

While employing the reflectometric method of measurement and the corresponding apparatus, the first stage in the procedure is to define the measuring scale by aid of one of several calibration measurements. In the calibration measurement, the measuring channels are first closed so that they are completely impermeable to light, for instance by means of a closing plate (not illustrated in the drawing). Simultaneously, the 0-value of the reference measuring device 21 is defined according to the equilibrium of the light intensities in the channels. Then the diaphragms 7, 17 of the channels 4, 14 are opened, whereafter the measuring diaphragm 17 of the reference channel 14 is set into a random position, for instance to an estimated position near the known reflectance value of the standard sample. Thereafter the diaphragm 7 of the measuring channel 4 is closed to such an extent that the channels are approximately in balance, i.e. that the light intensities in the channels are equal; the position of the diaphragm is registered in the central control unit. Then the measuring diaphragm 17 is adjusted to a position exactly corresponding to the balance of the light intensities in the channels, i.e. to a position where the reference measuring device 21 assumes the 0-value defined at the beginning; the position of the measuring diaphragm is registered in the central control unit. The determined set value conforming to the position of the measuring diaphragm now corresponds to the known reflectance value of the standard sample.

Figure 3:
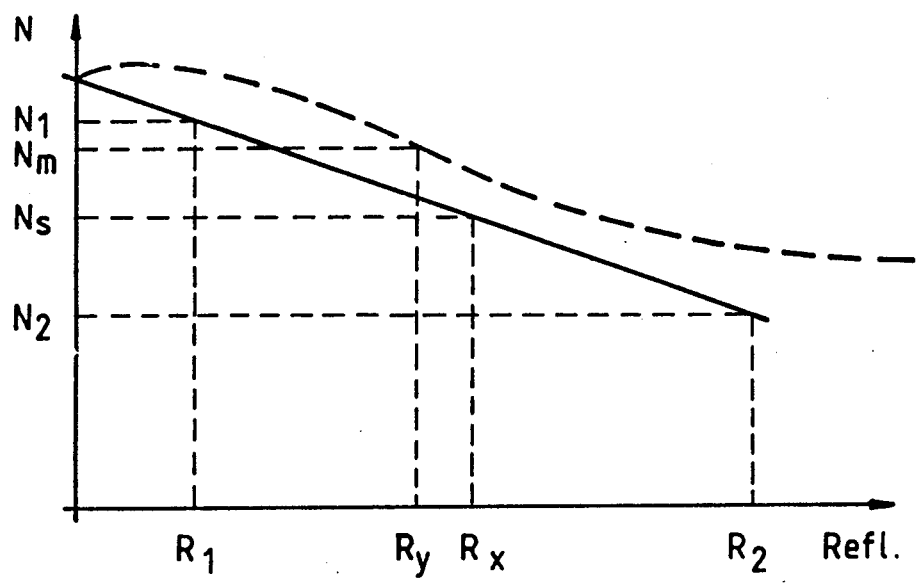
FIG. 3 illustrates the interdependence of the reflectance value and the linear scale in one measurement.

In a similar fashion, several standard measurements can be carried out with different standards, for instance with reflectance values between 0–100%. During these measurements, the diaphragm 7 of the measuring channel 4 is suitably maintained in the same position throughout, so that the dependence of the reflectance value on the position of the measuring diaphragm 17 is determined for instance in the form of a graph as is illustrated in FIG. 3 as a result of a series of measurements. Thereafter the sample measurement can be carried out quickly and easily by adjusting the diaphragm 7 of the measuring channel 4 to a position used in the calibration measurement and by determining the set values of the measuring diaphragm 17 of the reference channel 14 in equilibrium, according to what was said above. Now the reflectance values of the samples can be calculated on the basis of the calibration measurements.

If it is desired to examine the reflectance values of the samples at a certain wavelength, the central control unit 24 is directed to shift the desired and identical filters to both channels, for instance the filters 8 and 18, into the measuring channel and the reference channel respectively, as is illustrated in FIG. 1. The calibration measurements and the sample measurements are thereafter carried out by aid of filters for instance according to what is described above.

Figure 2:
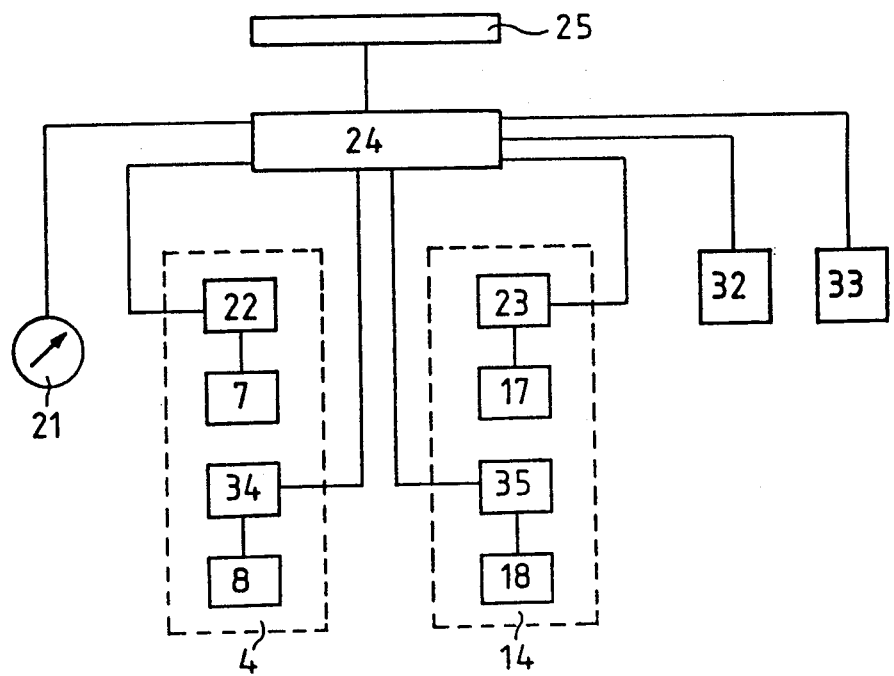

FIG. 2 shows a block diagram of the apparatus of the invention. Topmost is the keyboard 25 whereby the registering and calculating control unit, i.e. the computer, is controlled. The control unit 24 is arranged to control the actuator 22 of the diaphragm 7 of the measuring channel 4, and similarly the actuator 23 of the measuring diaphragm 17 of the reference channel 14. Furthermore, the control unit controls the actuators 34 and 35 of the filters 8 and 18 respectively, which shift the identical filters to each channel. Moreover, the control unit receives the measuring signals sent by the reference measuring device 21, on the basis of which signals the measuring diaphragm 17 of the reference channel 4 is controlled. In addition to this, in the described embodiment the control unit 24 controls the actuator 32 of the calibration samples, i.e. standard samples, and the shifting device 33 of the samples to be measured, so that it shifts the controlled standard samples and the samples to be measured to the aperture 3 of the measuring chamber 1.

Figure 4:
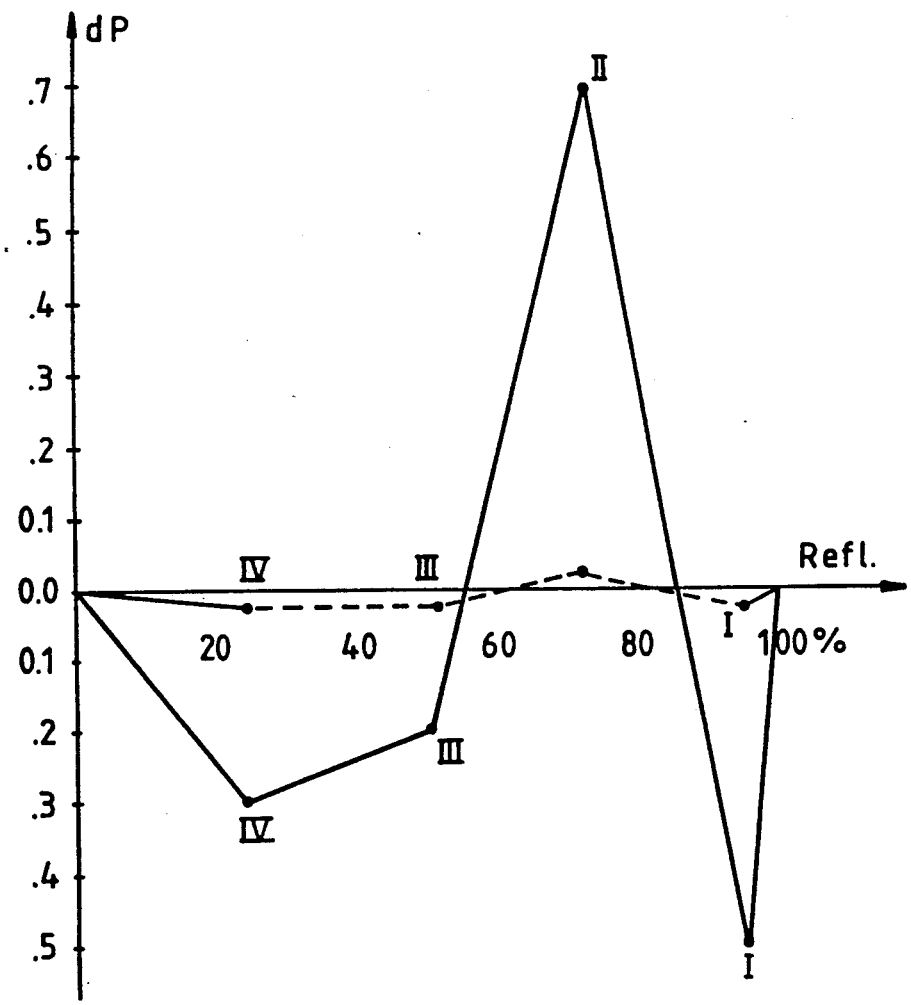
FIG. 4 shows the results from the measurements carried out by means of the method of the present invention as compared to those obtained from the measurements by means of the known Elrepho apparatus.

FIG. 4 is a graphic illustration of the measuring results from four measurements, where the measurements where carried out by means of an ordinary Elrepho apparatus (continuous line) and on the other hand by means of the apparatus of the invention as illustrated in FIG. 1 (dotted line) from samples with a known reflectance value. In both cases the calibration measurements were carried out as described above, and by employing the same known samples. From the measuring results it is apparent that the greatest error dP with the conventional method was 0.7% and with the method of the invention about 0.03%.

In the preferred embodiments, the employed actuators of the diaphragms 7 and 17 of the measuring channel 4 and the reference channel 14 respectively are stepping impulse motors. Instead of these, however, there can be used any type of precision motor such as a servomotor etc.

The reflectance value of the sample is determined from the measuring results for instance as is illustrated in FIG. 3 (continuous line), in case the reflectance value is or it is supposed to be linearly dependent on the set value N of the diaphragm of the reference channel. From FIG. 3 (continuous line) we obtain $$R_x = R_1 + (N_m - N_1)\frac{R_1 - R_2}{N_1 - N_2}$$

where $R_x$ is the reflectance value to be defined, $R_1$ and $R_2$ are reflectance values of the standard samples employed in the calibration measurements and $N_m$, $N_1$ and $N_2$ are set values of the reference channel obtained in the sample measurement and the calibration measurement respectively.

If the reflectance value is dependent on the set value of the diaphragm of the reference channel in a non-linear fashion (dotted line), the reflectance value $R_y$ to be defined can be determined graphically as is illustrated in FIG. 3 on the basis of the measured set value $N_n$ of the diaphragm of the reference channel.

The specified preferred embodiments of the method and apparatus of the invention are represented only as practical illustrations of the invention, and the modifications of the invention may be varied within the scope of the appended patent claims.

The measuring chamber may be, instead of ball-shaped, e.g. half ball-shaped or have another form.

The measuring chamber may have one or two or more light sources and it may emit light continuously or pulsed.

The filter of the measuring chamber may be a usual optic filter or e.g. a monochromator provided with for example a gate or a prism.

I claim:

1. A method of measuring the reflectometric properties of a sample by employing a 2-channel reflectometer having a measuring channel and a reference channel with each channel having a measuring diaphragm, comprising the steps of calibrating the reflectometer by placing a standard sample in the measuring channel, adjusting the light intensities in the measuring channel and the reference channel into balance through operation of the measuring diaphragm of the reference channel to provide a calibration measurement, placing a sample to be measured in the measuring channel, adjusting the light intensities in the measuring channel and the reference channel to balance by actuation of the measuring diaphragm in the reference channel, and calculating the reflective value of the sample to be measured by use of the set value of the measuring diaphragm of the reference channel from the reflectance value of the standard sample on the basis of the set value of the measuring diaphragm of the reference channel in the calibration measurement.

2. The method of claim 1, wherein the calibration step is characterized by defining the interdependence between the measuring scale of the measuring diaphragm of the reference channel and the reflectance to be measured in the measuring channel under measuring conditions by means of defining the set values of the measuring diaphragm through use of a plurality of standard samples while the diaphragm of the measuring channel is maintained in the same position.

3. The method of claim 1, wherein the light intensities in the measuring channel and the reference channel are detected through use of photometers and the light intensities in the measuring channel and the reference channel are compared by comparing voltages created by the light in the photometers through use of a reference measuring device.

4. The method of claim 3, wherein the zero-value of the reference measuring device corresponding to the balance of the light intensities is defined as a dark voltage value by providing both channels with a light-proof cover.

* * * * *